(12) United States Patent
Watrous

(10) Patent No.: US 6,629,937 B2
(45) Date of Patent: Oct. 7, 2003

(54) SYSTEM FOR PROCESSING AUDIO, VIDEO AND OTHER DATA FOR MEDICAL DIAGNOSIS AND OTHER APPLICATIONS

(75) Inventor: Raymond L. Watrous, Belle Mead, NJ (US)

(73) Assignee: Siemens Corporate Research, Inc., Princeton, NJ (US)

(*) Notice: Subject to any disclaimer, the term of this patent is extended or adjusted under 35 U.S.C. 154(b) by 240 days.

(21) Appl. No.: 09/753,162

(22) Filed: Jan. 2, 2001

(65) Prior Publication Data

US 2002/0052559 A1 May 2, 2002

Related U.S. Application Data

(63) Continuation-in-part of application No. 09/670,284, filed on Sep. 25, 2000, now Pat. No. 6,572,560.
(60) Provisional application No. 60/156,601, filed on Sep. 29, 1999.

(51) Int. Cl.$^7$ ................................................. A61B 7/04
(52) U.S. Cl. ........................ 600/586; 600/528; 128/920
(58) Field of Search ................................ 600/300, 528, 600/586; 128/906, 920, 923–925; 705/2–3; 607/30–32, 59–60

(56) References Cited

U.S. PATENT DOCUMENTS

| 3,846,585 A | 11/1974 | Slosberg et al. ........... 179/1 ST |
| 4,424,815 A | 1/1984 | Kuntz ........................ 128/715 |
| 4,446,873 A | 5/1984 | Groch et al. ................ 128/715 |

(List continued on next page.)

FOREIGN PATENT DOCUMENTS

WO    WO 96/13212    5/1996

OTHER PUBLICATIONS

Barschdorff et al., "Automatic Phonocardiogram Signal Analysis in Infants Based on Wavelet Transforms and Artificial Neural Networks", Computers in Cardiology 1995, Vienna Austria, Sep. 10–13, 1995, pp. 753–756.

(List continued on next page.)

Primary Examiner—Kennedy Schaetzle
Assistant Examiner—Kristen Droesch
(74) Attorney, Agent, or Firm—Donald B. Paschburg; F. Chau & Associates, LLP.

(57) ABSTRACT

A diagnostic decision support system provides diagnostic decision support for auditory evaluation of anatomical features and is applicable to virtually any living creature. The system processes an acoustic signal for medical applications by acquiring acoustic data representative of an acoustic signal associated with an anatomical function. The acquired acoustic data is stored in a file associated with a patient medical record. The acquired acoustic data and medical record information is automatically analyzed to determine physiologically significant features useful in medical diagnosis. Information is generated supporting medical diagnosis based on the automatic analysis. In addition, the analysis of the acquired acoustic data may be partially automatic and involve User input of information for use in facilitating diagnostic decision making. The system also processes patient identification information and acoustic test type information (e.g. identifying anatomical function, anatomical condition, auditory test anatomical location or patient posture).

28 Claims, 5 Drawing Sheets

U.S. PATENT DOCUMENTS

| | | | | |
|---|---|---|---|---|
| 4,528,689 A | | 7/1985 | Katz | 381/67 |
| 4,548,204 A | | 10/1985 | Groch et al. | 128/700 |
| 4,549,552 A | | 10/1985 | Groch et al. | 128/700 |
| 4,903,794 A | | 2/1990 | Klippert et al. | 181/131 |
| 4,905,706 A | | 3/1990 | Duff et al. | 128/701 |
| 5,010,889 A | | 4/1991 | Bredesen et al. | 128/715 |
| 5,012,815 A | | 5/1991 | Bennett, Jr. et al. | 128/715 |
| 5,025,809 A | | 6/1991 | Johnson et al. | 128/715 |
| 5,086,776 A | * | 2/1992 | Fowler et al. | 600/452 |
| 5,213,108 A | | 5/1993 | Bredesen et al. | 128/715 |
| 5,218,969 A | | 6/1993 | Bredesen et al. | 128/710 |
| 5,258,906 A | * | 11/1993 | Kroll et al. | 379/106.02 |
| 5,301,679 A | | 4/1994 | Taylor | 128/773 |
| 5,360,005 A | * | 11/1994 | Wilk | 600/437 |
| 5,420,382 A | | 5/1995 | Katz | 181/131 |
| 5,602,924 A | | 2/1997 | Durand et al. | 381/67 |
| 5,638,823 A | * | 6/1997 | Akay et al. | 600/501 |
| 5,685,317 A | | 11/1997 | Sjostrom | 128/715 |
| 5,687,738 A | * | 11/1997 | Shapiro et al. | 600/484 |
| 5,730,142 A | | 3/1998 | Sun et al. | 128/705 |
| 5,853,005 A | | 12/1998 | Scanlon | 128/662.03 |
| 5,860,933 A | | 1/1999 | Don Michael | 600/528 |
| 5,957,866 A | | 9/1999 | Shapiro et al. | 600/586 |
| 6,021,404 A | * | 2/2000 | Moukheibir | 600/501 |
| 6,048,319 A | | 4/2000 | Hudgins et al. | 600/528 |
| 6,053,872 A | | 4/2000 | Mohler | 600/485 |
| 6,083,156 A | | 7/2000 | Lisiecki | 600/301 |
| 6,105,015 A | | 8/2000 | Nguyen et al. | 706/26 |
| 6,120,442 A | | 9/2000 | Hickey | 600/300 |
| 6,135,966 A | | 10/2000 | Ko | 600/481 |
| 6,149,595 A | | 11/2000 | Seitz et al. | 600/438 |

OTHER PUBLICATIONS

Huiying et al., "A Heart Sound Feature Extraction Algorithm Based on Wavelet Decomposition and Reconstruction", Proc. Of the 20th Ann. Int'l Conf. of the IEEE Engineering in Medicine and Biology Society Hong Kong China, Oct. 29–Nov. 1 1998, vol. 20, No. 3, 1998, pp. 1539–1542.

Wu et al., "Computer–aided Analysis and Classification of Heart Sounds Based on Neural Networks and Time Analysis", 1995 Int'l Conf. on Acoustics, Speech and Signal Processing, Conf. Proceedings, vol. 5, 1995, pp. 3455–3458.

Edwards et al., "Neural Network and Conventional Classifiers to Distinguish Between First and Second Heart Sounds", IEE Colloquium on Artificial Intelligence Methods for Biomedical Data Processing, London, UK, Apr. 26, 1996, pp. 1–3.

Mangione, Salvatore et al., "Physical Diagnosis Skills of Physicians in Training: A Focused Assessment," *Academic Emergency Medicine*, 2:7 1995.

Mangione, Salvatore et al., "Cardiac Auscultatory Skills of Internal Medicine and Family Practive Trainees," *JAMA*, 278:9 1997.

Mangione, Salvatore et al., "The Teaching and Practice of Cardian Auscultation during Internal Medicine and Cardiology Training," *Ann Intern Med*, 119:47–54, 1993.

Padmanabhan, Vasant, et al., "Accelerometer Type Cardiac Transducer for Detection of Low–Level Heart Sounds," *IEEE Transactions on Biomedical Engineering*, 40:1, 1993.

Schwarts, Robert S. et al., "Improved phonocardiogram system based on acoustic impedance matching," *American Physiological Society*, 1980.

* cited by examiner

SYSTEM FOR PROCESSING AUDIO, VIDEO AND OTHER DATA FOR MEDICAL DIAGNOSIS AND OTHER APPLICATIONS

RELATED APPLICATION DATA

This application is a continuation-in-part application of non-provisional application Ser. No. 09/670,284 filed on Sep. 25, 2000 now U.S. Pat. No. 6,572,560 and claiming priority of provisional application Ser. No. 60/156,601, filed on Sep. 29, 1999.

BACKGROUND

1. Technical Field

The present system relates generally to medical systems for use in diagnosis and treatment.

2. Background Description

In the context of the rapidly increasing cost of health care, the role of the primary care physician as a gatekeeper to the resources of the medical system is critical. The challenge in using health care resources in a cost-effective manner is especially acute in diagnosis and treatment of heart conditions and other conditions involving the evaluation of sounds and murmurs.

The evaluation of sounds has importance in the diagnosis of a variety of medical conditions affecting, cardiac, gastro-intestinal, pulmonary and other anatomical systems. As an illustration, in cardiac diagnosis, the heart is listened to using a stethoscope. The primary heart sounds with reference to the sys/diastolic phase of the heart are identified. It is then determined whether there are any abnormal heart sounds present, such as murmurs and/or clicks. The relative loudness, duration, intensity pattern, spectral quality and time sequence of the heart sounds are assessed. The heart sounds are interpreted in terms of the physiological model of the action of the heart muscle, valves and chambers. A hypothesis is then developed about any possible disease states based on the acoustic evidence and knowledge of the patient's medical history. Possible diagnoses are differentiated by varying the placement of the microphone, the patient's posture, or by having the patient execute different maneuvers that accentuate or diminish certain heart sounds. The accumulated evidence is evaluated for the presence of heart disease. It is then decided whether to refer the patient for diagnostic imaging, particularly ultrasound.

A description of some of the many disadvantages of conventional auscultation of the heart follows. This description exemplifies difficulties in auditory evaluation of anatomical features in general. Auscultation of the heart is a difficult task, for many reasons. The stethoscope itself transfers only a small fraction of the acoustic signal at the chest surface to the listener's ears, and filters the cardiac acoustic signal in the process.

Much of the signal energy in many heart sounds is below the threshold of human hearing, and this situation only tends to worsen with increased age of the listener. Auscultation also relies on correctly determining the correspondence of the primary heart sounds with the systolic and diastolic phase of the heart, which is made more difficult when the systolic and diastolic intervals are more equal, typically at elevated heart rates. Auscultation also relies on detecting the correct sequence of brief events that are closely spaced in time, something that is difficult for human listeners.

Learning auscultation is also difficult because diagnostic instructional manuals rely on subjective descriptions of heart sounds, which require much practice to appreciate.

Furthermore, the practice and teaching of the clinical skill of auscultation of the heart has declined among physicians. Recent tests have demonstrated that physicians can identify reliably only a small number of standard heart sounds and murmurs, as described by Burdick et al., in "Physical Diagnosis Skills of Physicians in Training: A Focused Assessment", Acad. Emerg. Med., 2(7), pp. 622–29, July 1995; Mangione et al., in "Cardiac Auscultatory Skills of Internal Medicine and Family Practice Trainees: A Comparison of Diagnostic Proficiency", Journal of the American Medical Association, 278(9), pp. 717–22, September 1997; Gracely et al., in The Teaching and Practice of Cardiac Auscultation During Internal Medicine and Cardiology Training: A Nationwide Survey", Annals of Internal Medicine, 119(1), pp. 47–54, July 1997. Consequently, serious heart murmurs in many patients go undetected by physicians.

Furthermore, the decline in auscultation skills has led to an over-reliance on echocardiography, resulting in a large number of unnecessary and expensive diagnostic studies. As a result, reimbursement for echocardiography has recently come under scrutiny by Medicare. The problems described for cardiac diagnosis involving sound evaluation similarly apply to, gastro-intestinal, pulmonary and other anatomical systems.

Accordingly, it is desirable and advantageous to derive a system to support diagnostic decision making involving sound evaluation for use in human and animal diagnosis.

SUMMARY OF THE INVENTION

A diagnostic decision support system provides diagnostic decision support for auditory evaluation of anatomical features and is applicable to virtually any living creature. The system processes an acoustic signal for medical applications by acquiring acoustic data representative of an acoustic signal associated with an anatomical function. The acquired acoustic data is stored in a file associated with a patient medical record. The acquired acoustic data and medical record information is automatically analyzed to determine physiologically significant features useful in medical diagnosis. Information is generated supporting medical diagnosis based on the automatic analysis.

In another feature of the invention the analysis of the acquired acoustic data may be partially automatic and involve User input of information for use in facilitating diagnostic decision making.

In a further feature, the system processes patient identification information and acoustic test type information (e.g. identifying anatomical function, anatomical condition, auditory test anatomical location or patient posture).

DETAILED DESCRIPTION OF PREFERRED EMBODIMENTS

A diagnostic decision support system provides diagnostic decision support for auditory evaluation of anatomical functions. The system is applicable to humans and animals and any other organism generating sounds that may be usefully analyzed for diagnostic purposes. The system allows physicians to provide improved objectivity, accuracy and consistency of diagnoses of auditory signals alone or in combination with other medically significant signals. The system further provides either, a fully automatic diagnosis, or a partially automatic diagnosis involving processing of user entered factual information or information based on medical reasoning and judgement. The generated diagnosis comprises a list of clinical findings together with an indication of the probability that the findings are consistent with a particular medical condition (if a positive finding is made). The diagnosis may also identify further tests for which a patient may be usefully referred to refine the diagnosis, e.g., echocardiography following a cardiac examination. The system also allows both local operation (i.e., operation in the vicinity of a patient) and remote operation, at a user's discretion, by receiving and presenting information both locally and remotely, e.g. via the Internet. Thereby, the system enables health care providers to supply better health care to their patients at a lower cost, detect otherwise undiagnosed disease, reduce the costs of unnecessary referrals, and facilitate reimbursement for well-justified referrals.

It is to be understood that the present invention may be implemented in various forms of hardware, software, firmware, special purpose processors, or a combination thereof. In the described embodiment, the system is implemented in software as a program tangibly embodied on a program storage device. The program is uploaded and executed by a machine employing a suitable architecture. The machine is implemented on a computer platform having a central processing unit (CPU), a random access memory (RAM), and input/output (I/O) interfaces. The computer platform also includes an operating system and microinstruction code. The various processes and functions described herein may either be part of the microinstruction code or part of the program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures are implemented in software, the actual connections between the system components (or the process steps) may differ depending upon the manner in which the present invention is programmed.

Figure 1:
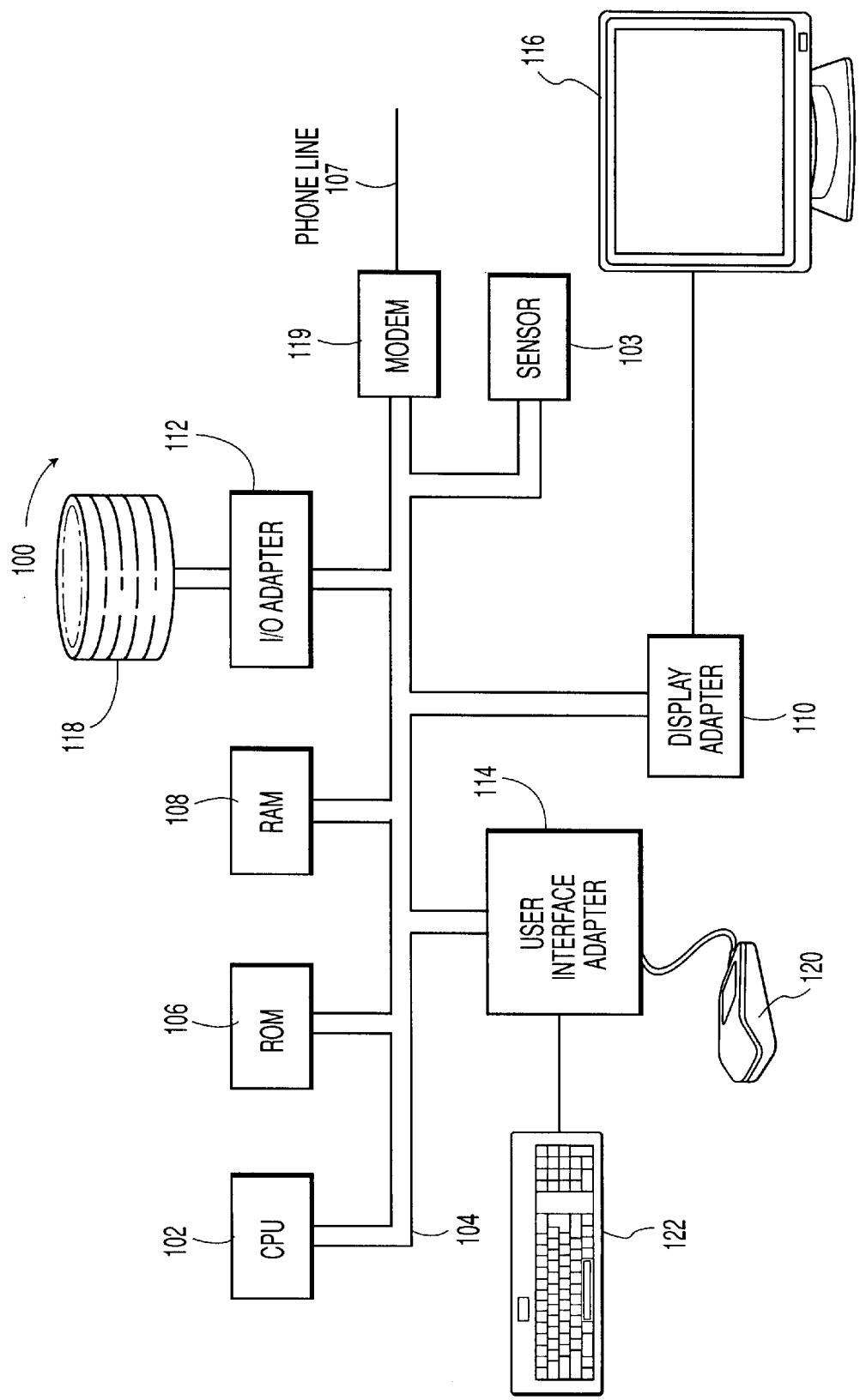
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. Further, a read only memory (ROM) 106, a random access memory (RAM) 108, a display adapter 110, an I/O adapter 112, and a user interface adapter 114 are operatively coupled to system bus 104.

A display device 116 is operatively coupled to system bus 104 by display adapter 110. A disk storage device (e.g., a magnetic or optical disk storage device) 118 is operatively coupled to system bus 104 by I/O adapter 112.

A mouse 120 and keyboard 122 are operatively coupled to system bus 104 by user interface adapter 114. The mouse 120 and keyboard 122 are used to input and output information to and from system 100. The system bus 104 is also coupled to modem 119 for Internet (or intra-net) communication via phone line 107 to enable system 100 to support both local and remote operation under the direction of processor 102. Bus 104 also provides bi-directional communication with sensor 103 to enable configuration and operation of the sensor and acquisition of acoustic data from the sensor.

The system is further described below in the context of processing an acoustic signal for a cardiac application. However, this is exemplary only, the system is also usable for diagnosis purposes of, for example, (a) pulmonary functions, (b) gastro-intestinal functions, (c) obstetrical and fetal functions (including use in conjunction with sonograms), (d) vocal functions, (e) skeletal joint function and other functions.

In a cardiac application, the system acquires cardiac acoustic signals from the chest surface, along with optional synchronized electrocardiogram and respiration signals. Moreover, user-provided information about the location of the acoustic sensor on the chest surface, postural information and any associated diagnostic maneuvers such as Valsalva are also acquired. The system analyzes these signals, extracts clinical findings, and generates an estimate of the probability of each of several heart diseases consistent with the clinical findings derived from the cardiac acoustic signal and patient medical record data. Based on these analyses, the system provides diagnostic decision support to the primary care physician in deciding whether to refer the patient for further diagnostic tests such as, for example, ultrasound.

The system provides documentation in the form of an annotated set of signals, which can be used to rationalize the referral decision. The system also supports interaction with the user that provides an explanation for the clinical findings and diagnostic recommendation. The acquired signals, extracted features, and interpretive and diagnostic results are archived for future reference, and can be made available electronically for data transfer via the Internet, or for generation of printed reports. An interface to hospital medical information systems for patient data transfer and telemedical applications is included. These functions may be embodied in a lightweight, handheld, signal acquisition unit and a portable analysis and display unit or in more stationary configurations, depending on the particular implementation of the system.

Various detailed descriptions of some of the elements of the system will now be given.

The first such element to be described is the sensor. The signal of interest is the cardiac acoustic waveform recorded on the chest surface. Preferably, the signal is recorded using an appropriate sensor having a high signal to noise ratio (SNR), good immunity to ambient noise and motion artifact, and excellent low-frequency response, to as low as 1 Hz. The surface cardiac acoustic signal is preamplified, and digitized for signal processing and interpretation.

One sensor for this purpose utilizes a fluid interface between the sensing element (a piezoelectric accelerometer) and the chest surface to achieve good impedance matching and an improved SNR. Such a sensor is described by: Padmanabhan et al., in "Accelerometer Type Cardiac Transducer for Detection of Low-level Heart Sounds", IEEE Transactions on Biomedical Engineering, 40(1), pp. 21–28, January 1993. The system is not limited to the preceding sensor and other sensors may be employed to record the cardiac acoustic waveform which maintain the spirit and scope of the inventive principles described herein.

The next element of the system which will now be described is signal processing. The acquired cardiac acoustic signal is filtered using standard methods to remove motion artifact and high frequency noise. The filtering is designed to preserve signal information at very low frequencies.

The filtered signal is analyzed using wavelet decomposition in order to extract time-frequency information. The kernel function of the wavelet decomposition is not critical to the invention. The wavelet decomposition is scaled to compensate for variations in amplitude. A set of cardiac acoustic features is extracted from the wavelet representation using adaptive neural networks. Features are detected corresponding to basic heart sounds such as, for example, S1, S2, murmur, and ejection click. These feature detectors are trained from data using labeled examples. The feature detectors operate continuously on the wavelet decomposition to produce a stream of feature data.

The extracted features are interpreted or parsed with reference to a state-transition model of the heart. The state machine can be probabilistic, such as, for example, a hidden Markov model. Of course, other techniques and/or state transition models may be employed to interpret or parse the extracted features, while maintaining the spirit and scope of the inventive principles.

The output of the state transition model allows determination of the cardiac phase of the signal, and subsequent identification of heart murmurs as systolic or diastolic. Other features, such as, for example, ejection clicks, M1, T1, A2 and P2 are identified and sequenced using the model.

The duration of any heart murmurs present is quantified relative to the systolic/diastolic interval, and the murmurs are labeled with reference to the phase as early-, mid-, late- or pan-systolic or diastolic. According to an illustrative embodiment of the invention, the murmur intensity is scaled by a psychoacoustic measure and graded I through VI. Of course, other measures and/or gradings may be used.

The clinical findings derived by signal processing are provided as input to the signal classification module.

The following element of the system which will now be described is the user interface (acoustic sensor). The position of the acoustic sensor on the chest surface is an important parameter in auscultation.

The sensor position can be inferred with respect to a standard site sequence protocol, guided by the signal interpretation system, confirmed by the user, input by the user using a keyboard, mouse, or position indicator located on the acoustic sensor, or measured with reference to a standard location by a position sensor.

The patient's posture is also an important parameter of auscultation that can be provided by the user, along with any dynamic auscultation maneuvers associated with the signals being acquired at the time.

Another element of the system which will now be described is the diagnostic decision support element. The clinical findings derived by processing the cardiac acoustic signal are provided, along with available relevant patient medical record data, as inputs to a probabilistic reasoning network that is used to compute an estimate of the indication of need for echocardiography referral. The probabilistic reasoning network also estimates the posterior probabilities of cardiac diseases. The output of the probabilistic reasoning network is presented to the user as referral recommendation probability along with a rank-ordered list of the most probable cardiac diseases.

The probabilistic network can also be used to generate explanations to the user at various levels of detail in support of the diagnostic and referral recommendations.

A description of various extensions and alternatives will now be given with respect to the sensors employed by the system, as well as applications of the system.

The surface electrocardiogram can optionally be recorded to provide a reference signal for synchronizing the recorded acoustic signal. The recorded ECG need only comprise a single channel, requiring a single electrode and electrical reference.

A respiration signal can also be optionally recorded in order to provide information about the respiratory activity of the patient for use in the interpretation of the cardiac acoustic signal. The respiratory signal can be obtained from, for example, impedance respiration or nasal thermistor sensors.

A pulse oximetry signal can also be optionally recorded to provide information about the cardiac activity of the patient for use in the interpretation of the cardiac acoustic signal. The pulse oximetry signal can be obtained from, for example, a photoplethysmographic sensor, typically applied to the finger tip.

A pressure sensor can also be optionally incorporated with the acoustic sensor to measure the application pressure of the acoustic sensor to the chest surface. This sensor can be used to detect instances where the application pressure is too low or too high; if the pressure is too low, the acquired signal amplitude will be low, whereas too high a pressure will create a diaphragm of the surface skin and result in modified spectral properties.

A position sensor can also be optionally incorporated with the acoustic sensor to measure the position of the acoustic sensor with respect to some reference point. Alternatively, a position indicator can be included on the sensor head to allow the user to indicate the current position, or to advance the current position according to a specific sensor position sequence.

With respect to extensions and applications of the system, computer-assisted auscultation could be applied to other anatomical sites, such as the carotid arteries or other arteries, and used to evaluate other sound types, such as pulmonary and gastrointestinal, with respect to different corresponding disease categories.

The system could be applied to the evaluation of the status of artificial heart valves and for assessment of the associated thrombolytic risk. The system could be applied to other animals, such as those encountered in veterinary practice.

Other users could find use for the system, such as dentists deciding whether to prescribe prophylactic antibiotics, less highly trained medical personnel involved in cardiovascular screening, such as medics screening inductees for military service, or nurses conducting preparticipation screening for high school/college sports.

The system could also be used in routine screening of critical personnel, such as pilots, public transit drivers, police and emergency first responder personnel.

Figure 2:
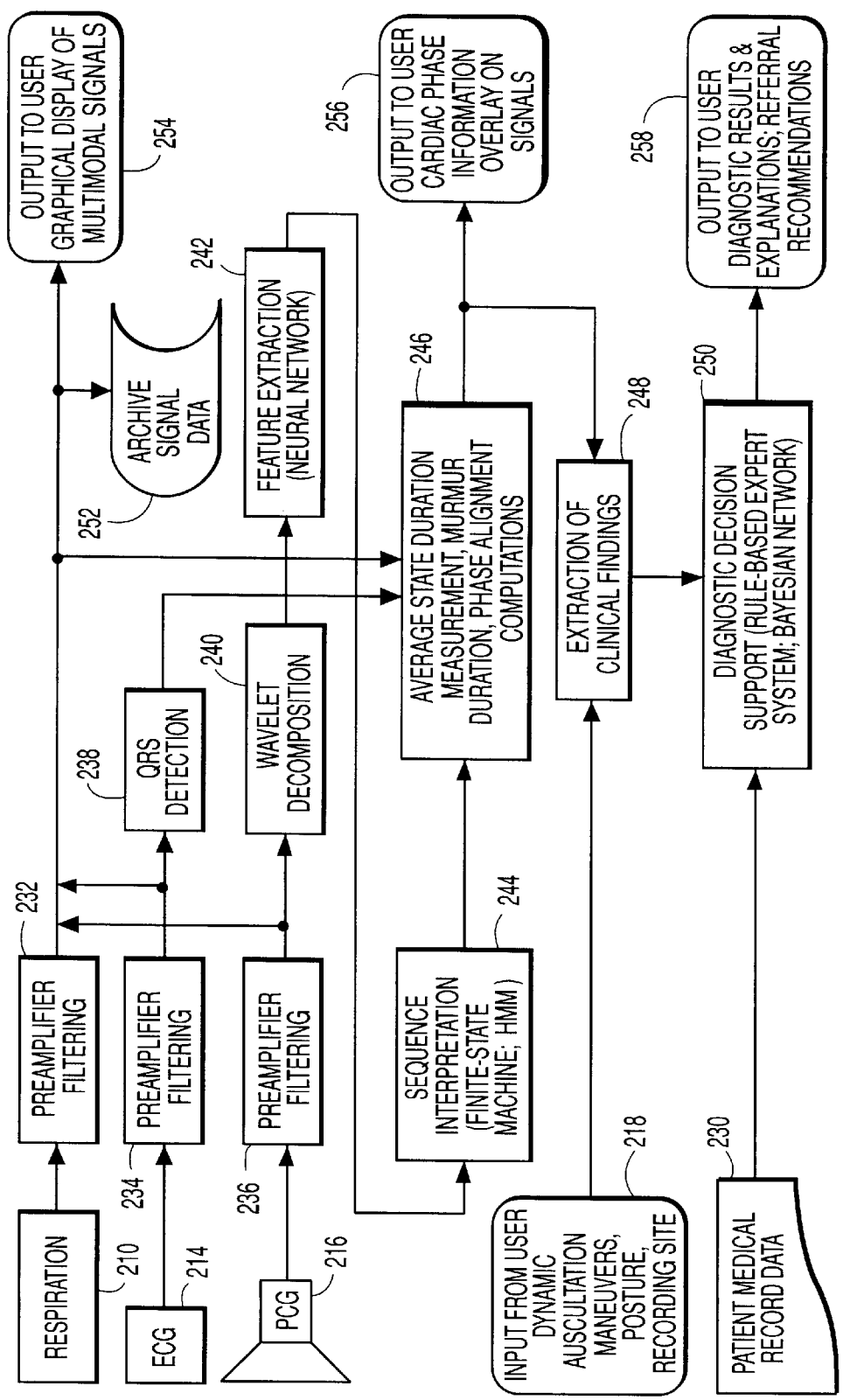
FIG. 2 is a high level block diagram illustrating a multi-modal cardiac diagnostic decision support system/method, according to an illustrative embodiment of the invention.

FIG. 2 is a high level block diagram illustrating a multi-modal cardiac diagnostic decision support system/method, according to an illustrative embodiment of the system.

A respiration sensor 210 may optionally be employed to record a respiration signal. The respiration signal can be used to provide information about the respiratory activity of the patient for use in the interpretation of the cardiac acoustic signal. The respiratory signal can be obtained from, for example, an impedance respiration sensor or a nasal thermistor sensor. An electrocardiogram (ECG) sensor 214 may optionally be employed to record the surface electrocardiogram to provide a reference signal for synchronizing the recorded acoustic signal. The recorded ECG need only comprise a single channel, requiring a single electrode and electrical reference. A PCG (phonocardiogram) sensor 216 may be used to record the cardiac acoustic waveform on the chest surface.

The PCG sensor 216 should have a high signal to noise ratio, good immunity to ambient noise and motion artifact, and excellent low-frequency response, to as low as 1 Hz. The surface cardiac acoustic signal is preamplified, and digitized for signal processing and interpretation. One sensor for this purpose utilizes a fluid interface between the sensing element (a piezoelectric accelerometer) and the chest surface to achieve good impedance matching and an improved SNR. This sensor is described by Barnes et al., in "Improved Phonocardiogram System Based on Acoustic Impedance Matching", Am. J. Physiol., 238(4):H604-9, April 1980.

Dynamic input 218 corresponding to the patient is received. Information about the patient's posture, site of PCG recording, along with any dynamic auscultation maneuvers associated with the signals being acquired at the time is input to the system using either a hand-held device that incorporates positional indicators, buttons and actuators or a combination of keyboard and mouse actions from a PC.

Patient Medical Data input 230 is also received. Medical information about the patient, including symptoms, history and results of physical examination, are entered into the diagnostic system in electronically readable form from a Smart card or other computer-based data source.

A respiration preamp & filter 232 is employed to amplify and filter the respiration using standard methods, to, e.g., increase the signal to noise ratio.

An ECG Preamp & Filter 234 is employed to amplify and filter the ECG signal using standard methods to, e.g., increase the signal to noise ratio.

A PCG Preamp & Filter 236 is employed to amplify and filter the PCG signal using standard methods to, e.g., increase the signal to noise ratio.

A QRS detection circuit 238 is employed to detect the QRS event in the ECG signal using standard methods. Note, QRS is the designation of a complex of three events in the ECG signal, closely spaced in time, which correspond to the onset of ventricular systole (contraction). The output of the QRS detection circuit 238 provides synchronization information for the interpretation of the phonocardiogram.

A wavelet decomposition circuit 240 is employed to analyze the filtered signal using wavelet decomposition to extract time-frequency information. The kernel function of the wavelet decomposition is not critical to the invention and, thus, any kernel function may be used while maintaining the spirit and scope of the invention. In a preferred embodiment of the system, the wavelet employed is a Morlet wavelet. The wavelet decomposition is preferably scaled to compensate for variations in amplitude.

Neural network feature extractors 242 are trained from labeled examples to identify basic heart sounds, clicks and murmurs. In a preferred embodiment, the neural networks are of the time-delay variety, where the input span, number of layers, unit function, connectivity and initial weight selection are appropriately chosen according to well-known methods. However, it is to be appreciated that other types of neural networks may be used in accordance with the invention, while maintaining the spirit and scope thereof.

A sequence interpreter 244 interprets or parses the extracted features with reference to a state-transition model of the heart to determine the most probable sequence of cardiac events. The state machine can be probabilistic, such as, for example, a hidden Markov model. However, other types of state transition models may be used which maintain the spirit and scope of the inventive principles.

A duration & phase measurement circuit 246 computes the average state durations of the sequence model. Event sequences are read off from the state trajectory of the sequence model.

A clinical findings extractor 248 extracts clinical findings from the acoustic signal based on the state duration, phase and amplitude information, along with dynamic and positional information provided by the user. Any heart murmurs present are quantified relative to the systolic/diastolic interval, and the murmurs are labeled with reference to the phase as early-, mid-, late- or pan-systolic or diastolic. The murmur intensity is scaled by a psychoacoustic measure and graded I through VI.

A decision support circuit 250 combines clinical findings with patient medical data input to produce estimates of the posterior probabilities of the covered cardiac diseases. This involves Bayesian networks and expert systems. Dynamic Bayesian networks can be used to model the progress of disease states.

An archive signal data store 252 archives recorded signals for later reference and display use. Preferably, the store 252 is an electronic or optical storage medium.

A signal output device 254 presents the recorded signals to the user. The signal output device 254 may be, for example, a display device (e.g., PC monitor, hand-held LCD, etc.) or printer. The output waveforms are identified and scaled according to factors selectable by the user.

An analysis output device 256 provides the results of the analysis of the acoustic signal to the user. The analysis output device 256 may be, for example, a display device (e.g., computer monitor, hand-held LCD, etc.) or printer. The analysis output may be in graphical form, and may be overlaid on the signal output (waveform data). Systolic and diastolic phase, and heart murmurs may be highlighted using an intuitive color-coded scheme.

A diagnostic output device 258 provides the results of the diagnostic decision support analysis to the user. The diagnostic output device 258 may be, for example, a display device (e.g., computer monitor, hand-held LCD, etc.) or printer. The diagnostic output may be in text form, and may include explanatory information and references to graphically displayed data. Most informative next tests or procedures are identified. The level of explanatory detail is selectable by the user.

Figure 3:
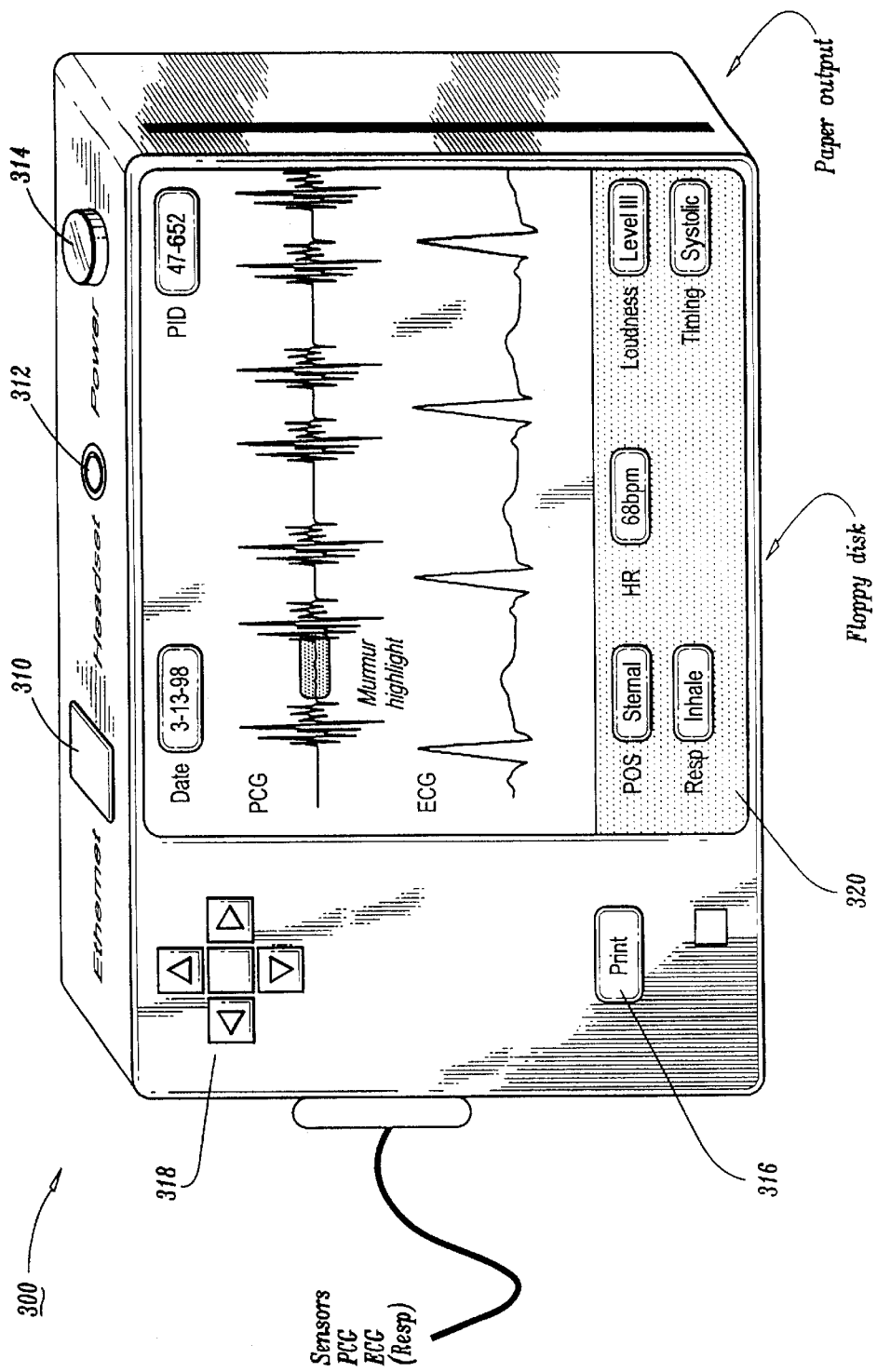
FIG. 3 is a diagram illustrating a portable cardiac diagnostic decision support system 300, according to an illustrative embodiment of the invention.

FIG. 3 is a diagram illustrating a portable cardiac diagnostic decision support system 300, according to an illustrative embodiment of the system. The system 300 contains an Ethernet interface 310, a headset jack 312, a power switch 314, a print button 316, and a direction keypad 318. On a display 320 is shown the date, patient ID, PCG signal, ECG signal, POS, respiration state, heart rate, loudness setting, and cardiac timing. The system 300 includes a floppy drive for receiving a floppy disk, and a printer with paper output.

Figure 4:
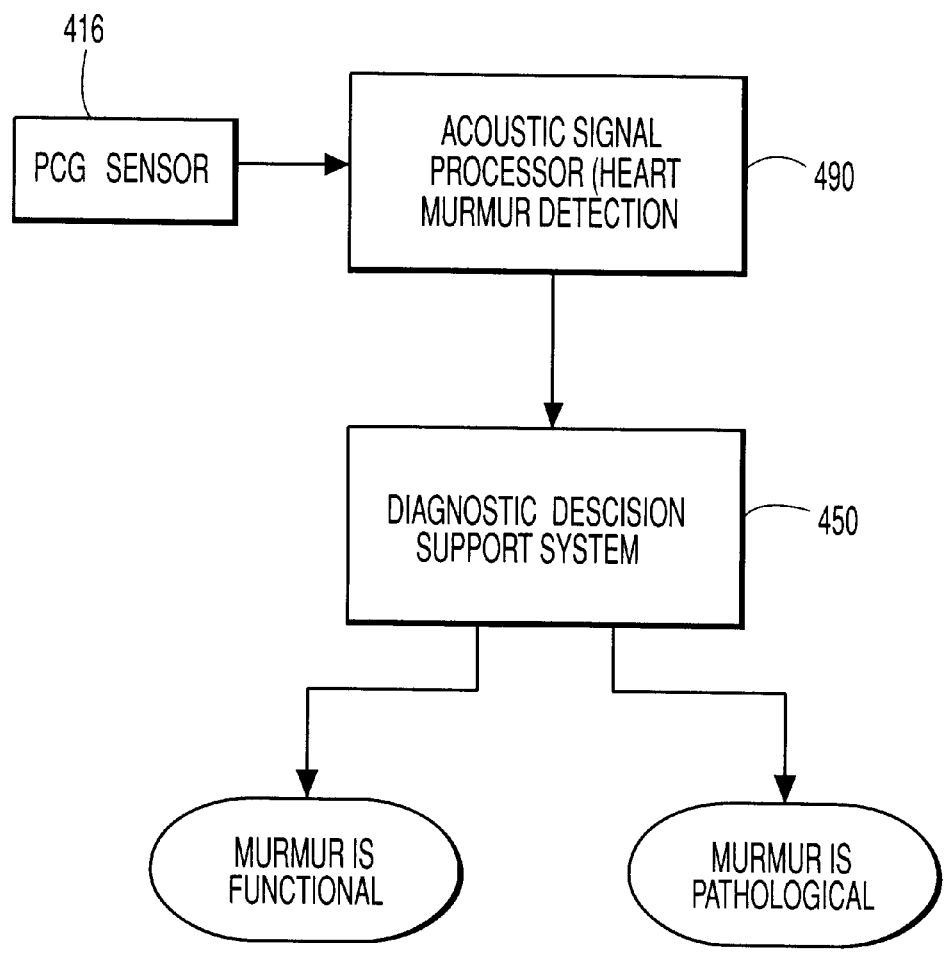
FIG. 4 is a high level block diagram illustrating a system/method for determining a status of heart murmurs, according to an illustrative embodiment of the invention.

FIG. 4 is a high level block diagram illustrating a system/method for determining a status of heart murmurs, according to an illustrative embodiment of the system. A PCG sensor 416 obtains the cardiac acoustic waveform on the chest surface. An acoustic signal processor 490 detects a murmur, if any, from the cardiac acoustic signal. A diagnostic decision support system 450 determines whether the murmur is functional or pathological, based upon expert rules.

A description of some of the various elements of the system will now be given. In this embodiment, a neural network is used for extraction of physiologically significant features from the processed cardiac acoustic signal. These features correspond to basic heart sounds, such as S1, or their components, such as M1, T1, murmurs, and so forth. In other embodiments other types of processing system may be used to extract the physiologically significant features. This system embodiment also employs the combination of wavelet processing of the phonocardiogram with neural network feature extraction. In addition, the system processes a feature string by a probabilistic finite-state automaton to parse the cardiac acoustic signal to determine a most probable sequence of cardiac events given the received cardiac acoustic signal. The system extracts clinical findings from the interpreted (parsed) cardiac acoustic signal, such as those employed in expert auscultation of the heart, including intensity, intensity profile, duration, time-alignment, sequence and spectral quality features, and so forth. Moreover, the system implements a diagnostic decision function using Bayesian networks in which the probability of cardiac diseases being present, given the evidence of clinical findings, is derived from the results of signal processing and the patient medical record information. Additionally, the system determines whether a detected murmur is functional or pathological on the basis of expert rules.

A description of some of the numerous advantages of the system over manual auscultation of the heart will now be given. Using a specially designed sensor, the system acquires a cardiac acoustic signal with much greater fidelity and at higher signal amplitude than is possible with the standard stethoscope. The signal acquisition and processing system is sensitive to broader range of frequencies than the unassisted human listener. The device is sensitive to frequencies outside the range of human hearing which contain significant diagnostic information for the evaluation of cardiac status and the diagnosis of cardiac disease. The system is able to synchronize heart sounds with the diastolic/systolic phases of the heart, even under circumstances such as elevated heart rate, which make this task difficult for human listeners.

The system provides an objective measure of murmur intensity that can be normalized to compensate for human psychoacoustics. The system provides an objective measure of murmur duration, murmur frequency content, murmur phase and intensity profile. The system interprets the sequence of heart sounds probabilistically using a statistical model of heart sound generation. Using digital signal processing techniques, the system can distinguish the identity and sequence of brief heart sounds that are separated by short time durations.

The system extracts clinical findings from a cardiac acoustic signal using adaptive nonlinear methods. The system integrates statistical signal processing with probabilistic reasoning in a unified model (Bayesian network). The probabilistic reasoning model supports explanation of diagnostic recommendations. The system provides documentation of the cardiac acoustic signal and its interpretation, in the form of an archival record of the signal, the analysis of the signal, and the interpretation of signal in the context of the patient medical record data. The signal acquisition, processing and interpretation provides support and rationalization for the decision to refer for more expensive diagnostic tests, typically diagnostic imaging such as ultrasound.

Figure 5:
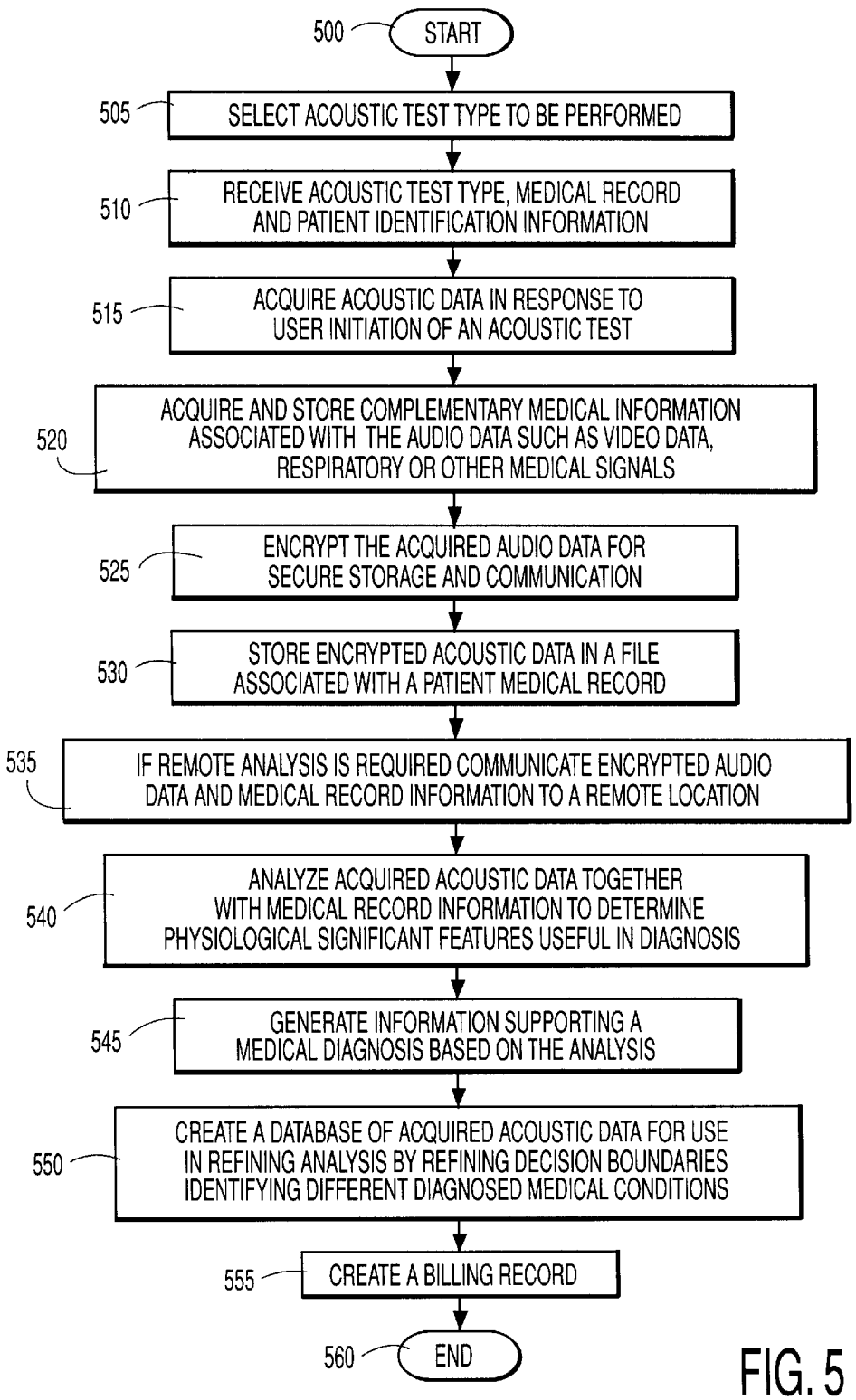
FIG. 5 is a flowchart of a process employed by the system of FIGS. 1–3 for processing acoustic data according to invention principles.

FIG. 5 shows a flowchart of a method employed by the system of FIGS. 1–3 for processing acoustic data. In the system of FIG. 1, for example, the method of FIG. 5 is employed by processor 102 in directing system 100 to process acoustic data for analysis of a variety of anatomical functions. In step 505, following the start at step 500, processor 102 (FIG. 1) selects an acoustic test type to be performed in response to User entered test selection data. In step 510, processor 102 receives and stores acoustic test type, medical record and patient identification information. The test type data identifies the anatomical function being examined (e.g., cardiac, pulmonary, gastro-intestinal, gynecological, skeletal etc.). The test type data also identifies the conditions of the test including specific locations of the organ or body part under examination as well as the condition of the patient and his posture or activity during the test and includes sensor related data. In step 515, processor 102 acquires acoustic data in response to User initiation of an acoustic test and in step 520 also acquires complementary medical information associated with the audio data. The complementary medical information may include video data (representing a sonogram or MRI (Magnetic Resonance Image), for example), or respiratory, temperature, blood pressure, oximetry, or electrical sensory signals or other medically significant signals of value in diagnosis. Information supporting synchronized reproduction of the complementary signals together with the audio data is also acquired. The synchronization information enables analysis based upon combined signal data and synchronized replay of the audio data and a corresponding video picture or other signal on a medical workstation, for example. In step 525, processor 102 encrypts and compresses the acquired audio data (and the other acquired medical record and complementary signal data, as required) for secure storage, in step 530, in a file associated with a patient medical record. The encrypted and compressed data is also available for secure communication to a remote location.

In step 535, processor 102 determines whether a local or remote analysis application is required. If a remote application is required, processor 102 directs system 100 (FIG. 1) in communicating the encrypted acoustic data, medical record information and complementary medical information to a remote location for analysis. The acquired acoustic data and other data is communicated to a remote location via the Internet or an intra-net or other communication network. If a local analysis application is required, processor 102, in step 540, analyzes the acquired acoustic data, medical record information and complementary medical information for physiologically significant features to determine clinical findings and recommended courses for further action. The analysis is done using the advantageous principles identified in connection with FIGS. 1–4. The analysis may include, for example, a comparison of a patient's acoustic data with previously obtained acoustic data (e.g. obtained 6 months or some other period earlier) retrieved from storage. The system discloses to a User the conditions under which the previous test was performed to enable a directly comparable test to be performed this time and warns a User if there is a test condition incompatibility. Further, in the case of either the remote analysis application or local analysis application, the analysis may be either fully automatic or may be partially automatic. If the analysis is partially automatic, it involves User input of factual or opinion related information via menu screens in order to supplement or direct the analysis process. Thereby the system supports diagnosis of acquired acoustic data and other data by either, a local operative (a physician or nurse, for example) acting alone or in conjunction with a remotely located expert. In the latter case, the remotely located expert enters clinical opinion and related data via menu screens following his analysis of the acoustic and other data received via the Internet, for example.

In step 545, processor 102 directs system 100 in generating and presenting information to a User supporting a medical diagnosis based on the analysis performed in step 540. Processor 102 directs system 100 in generating a list of clinical findings together with other findings derived from the medical record. In addition, a conclusion identifying the determined clinical findings as being consistent with one or more medical conditions may be provided. Further, such listed medical conditions may be ranked according to likelihood of occurrence, or combined with an associated estimate of likelihood of occurrence. The generated information may also include identification of options for further diagnosis or treatment depending on the condition analyzed. The options for further diagnosis or treatment are ranked according to cost-effectiveness but, in other embodiments, may be ranked according to other criteria such as cost or the informative value of the recommended course of action or may not be ranked at all.

In step 550, processor 102 creates a database of acquired acoustic data, complementary medical data and associated patient medical information and employs this database to improve the analysis and diagnosis process. This is done by comparing previously automatically (and partially automatically) generated analyses of clinical findings and diagnosed conditions with the corresponding acquired data and any additional data such as independently verified findings subsequently acquired and entered into the database. Thereby, processor 102 is able to use this database and independent findings in auditing previously generated analyses and in refining decision boundaries that identify different medical conditions. This enables improvement of the analytical process, increases the system value over time and provides a mechanism for continuously adapting the system in accordance with new developments in diagnostic knowledge and test procedures. In step 555, processor 102 directs system 100 in creating a billing record for billing a patient and associated insurance company. This is done using previously acquired patient insurance information, as well as information defining the type of diagnosis and acoustic test performed and whether or not the test is exclusively performed locally or involves remote data input by an expert in the field. The process of FIG. 5 terminates at step 560.

Although the illustrative embodiments have been described herein with reference to the accompanying drawings, it is to be understood that the present system and method is not limited to those precise embodiments, and that various other changes and modifications may be implemented by one skilled in the art without departing from the scope or spirit of the system. All such changes and modifications are intended to be included within the scope of the invention as defined by the appended claims.

What is claimed is:

1. A program storage device readable by machine, tangibly embodying a program of instructions executable by the machine to perform method steps for processing an acoustic signal for medical applications, the method steps comprising:

receiving acoustic test type identification information;

acquiring acoustic data representative of an acoustic signal associated with an anatomical function;

storing said acquired acoustic data in a file associated with a patient medical record;

performing an analysis to determine physiologically significant features useful in medical diagnosis using said acquired acoustic data and medical record information, wherein said analysis is partially automatic and comprises generating a menu during said analysis to prompt user input of information that is used for facilitating diagnostic decision making and directing said analysis; and generating information supporting medical diagnosis based on said analysis.

2. The program storage device according to claim 1, wherein the instructions for performing said analysis comprises instructions for examining at least one of (a) audio level intensity, (b) intensity profile, (c) duration, (d) time-alignment, and (e) sequence and spectral quality features.

3. The program storage device according to claim 1, wherein said acoustic test type identification information identifies as least one of, (a) anatomical part or function being investigated, (b) the condition of said anatomical part of function being investigated, (c) the location on the anatomy where said acoustic test is performed and (d) patient posture or activity occurring during acquisition of said acoustic data.

4. The program storage device according to claim 1, including instructions for performing the step of creating a billing record for a diagnosis, said record identifying a type of acoustic test performed.

5. A program storage device readable by machine, tangibly embodying a program of instructions executable by the machine to perform method steps for processing an acoustic signal for medical applications, the method steps comprising:

acquiring acoustic data representative of an acoustic signal associated with an anatomical function;

storing said acquired acoustic data in a file associated with a patient medical record;

automatically analyzing said acquired acoustic data and medical record information to determine physiologically significant features useful in medical diagnosis; and generating information supporting medical diagnosis based on said automatic analysis, wherein said generating step comprises generating an identification of options for further diagnostic tests ranked according to at least one of cost, cost effectiveness and informative value of the test.

6. A method for processing an acoustic signal for medical applications, comprising the steps of:

acquiring acoustic data representative of an acoustic signal associated with an anatomical function;

storing said acquired acoustic data in a file associated with a patient medical record;

automatically analyzing said acquired acoustic data and medical record information to determine physiologically significant features useful in medical diagnosis; and generating information supporting medical diagnosis based on said automatic analysis, wherein said generating step comprises generating an identification of options for further diagnostic tests ranked according to at least one of cost, cost effectiveness and informative value of the test.

7. The method according to claim 1, including the step of, receiving patient identification information and medical record information.

8. The method according to claim 1, wherein said acoustic data representative of an acoustic signal is associated with at least one of, (a) cardiac function, (b) pulmonary function, (c) gastro-intestinal function, (d) obstetrical and fetal function (e) vocal function, and (f) skeletal joint function.

9. The method according to claim 1, wherein said step of generating information supporting medical diagnosis comprises generating at least one of, (a) a list of clinical findings, (b) a list of clinical findings together with other findings derived from said medical record, (c) a conclusion identifying determined clinical findings as being consistent with one or more medical conditions, and (d) an identification of an option for further diagnosis or treatment.

10. The method according to claim 1, wherein said step of generating information supporting medical diagnosis comprises generating a list of one or more potential medical conditions wherein said list includes medical conditions that are at least one of, (a) ranked according to likelihood of occurrence, and (b) combined with an associated estimate of likelihood of occurrence.

11. The method according to claim 1, including the steps of encrypting said acquired acoustic data; and communicating said encrypted acquired acoustic data to a remote location in response to a data request.

12. The method according to claim 11, wherein, said communicating comprises secure communication on one of (a) an Intranet and (b) the Internet and said encrypting and communicating steps include encrypting and communicating medical record information as well as said acoustic data.

13. The method according to claim 11, wherein, said step of automatically analyzing said acquired acoustic data is performed at said remote location.

14. The method according to claim 1, including the steps of acquiring and storing additional medically significant data associated with said acquired acoustic data together with information supporting retrieval of said additional medically significant data and audio data for synchronized reproduction.

15. The method according to claim 14, wherein said additional medically significant data comprises at least one of, (a) video data, (b) a sonogram, (c) a respiratory signal, (d) a temperature signal, (e) a blood pressure signal, (f) electrical activity signal and (g) a pulse oximetry signal.

16. The method according to claim 1, including the step of creating a database of acoustic data and associated patient medical information.

17. The method according to claim 16, including the step of improving said analyzing step by using said database in refining a decision boundary identifying different medical conditions.

18. The method according to claim 6, including the step of creating a billing record for billing for a diagnosis based on at least one of, (a) patient insurance information, (b) type of diagnostic test performed and (c) whether said acoustic data is locally generated or received from a remote location.

19. The method according to claim 1, wherein the step of automatically analyzing comprises comparing said acquired acoustic data to previously acquired acoustic data derived under comparable conditions.

20. A method for processing an acoustic signal for medical applications, comprising the steps of:

receiving patient identification information and medical record information;

acquiring acoustic data representative of an acoustic signal associated with an anatomical function;

storing said acquired acoustic data in a file associated with a patient medical record;

performing an analysis to determine physiologically significant features useful in medical diagnosis using said acquired acoustic data and medical record information, wherein said analysis is partially automatic and comprises generating a menu during said analysis to prompt user input of information that is used for facilitating diagnostic decision making and directing said analysis; and generating information supporting medical diagnosis based on said analysis.

21. The method according to claim 20, including the step of communicating said menu to a remote location, wherein said user input of information occurs at said remote location.

22. The method according to claim 20, including the step of communicating said acquired acoustic data and medical record information to a remote location, and said analyzing step is performed at least in part at said remote location.

23. The method according to claim 20, including the step of conditioning said acquired acoustic data for secure storage.

24. The method according to claim 20, including the step of, securely communicating said acquired acoustic data to a remote location in response to a data request.

25. The method according to claim 20, including the steps of, initiating acquisition of said acoustic data in response to a user command, and receiving information identifying a type of acoustic data acquired.

26. The method according to claim 25, wherein, said information identifying type of acoustic data identifies at least one of, (a) anatomical part or function being investigated, (b) the condition of said anatomical part or function being investigated, (c) the location on the anatomy where said acoustic test is performed, and (d) patient posture or activity occurring during acquisition of said acoustic data.

27. The method according to claim 26, including the step of, selecting an acoustic test to be performed and determining type of acoustic data acquired.

28. The method according to claim 20, including the step of creating a billing record for billing for a diagnosis, said record identifying a type of acoustic test performed.

* * * * *

UNITED STATES PATENT AND TRADEMARK OFFICE
CERTIFICATE OF CORRECTION

PATENT NO. : 6,629,937 B2  
DATED : October 7, 2003  
INVENTOR(S) : Raymond L. Watrous It is certified that error appears in the above-identified patent and that said Letters Patent is hereby corrected as shown below:

Column 12,
Line 65, please delete "1" and insert -- 6 --.

Column 13,
Lines 1, 6, 16, 24, 39 and 51, please delete "1" and insert -- 6 --.

Column 14,
Line 1, please delete "1" and insert -- 6 --.

Signed and Sealed this

Second Day of August, 2005

JON W. DUDAS
*Director of the United States Patent and Trademark Office*